United States Patent [19]

Smith et al.

[11] Patent Number: 4,856,351
[45] Date of Patent: Aug. 15, 1989

[54] SAMPLE CHAMBER AND SYSTEM FOR ANALYZING FLUID INCLUSIONS

[75] Inventors: Michael P. Smith; Frank C. Haines, Jr., both of Tulsa, Okla.

[73] Assignee: Amoco Corporation, Chicago, Ill.

[21] Appl. No.: 114,349

[22] Filed: Oct. 27, 1987

[51] Int. Cl.$^4$ .......................... G01N 1/10; G01N 1/28; G01N 33/24
[52] U.S. Cl. ................................. 73/863.21; 73/864; 73/874.41; 73/864.91; 356/36
[58] Field of Search ................ 73/863.21, 864.51, 864, 73/864.41, 864.91, 866, 863; 356/36, 244; 436/32; 250/288 R, 428

[56] References Cited

U.S. PATENT DOCUMENTS

| | | | |
|---|---|---|---|
| 3,987,677 | 10/1976 | Alter | 73/19 |
| 4,152,941 | 5/1979 | Abou-Sayed et al. | 73/804 X |
| 4,613,755 | 9/1986 | Hudgens | 250/282 |
| 4,625,573 | 12/1986 | Henry | 73/864.44 |

OTHER PUBLICATIONS

"Liquid Inclusions in Minerals as a Geologic Barometer"; pp. 181–195; *International Geology Review;* 1955; V. A. Kalyuzhnyy (translated by V. P. Sokloff).
"Chemical Composition of Liquid Inclusion in Iceland Spar and Genetic Problems"; *Geochemistry*, No. 3; pp. 269–278; 1958; N. I. Khitarov et al.
"The Analysis of Fluid Inclusions in Halite"; *Geochemica and Cosmochemica Acta;* vol. 52; pp. 485–490; 1988; Boaz Lazar et al.
"Mass Spectrometric Determination of Gases in Individual Fluid Inclusions in Natural Minerals"; *Anal. Chem.,* vol. 58, No. 7, pp. 1330–1333; Colin Barker et al.; Jun. 1986.
*Reviews in Mineralogy*, vol. 12, "Fluid Inclusions"; pp. 109, 117 & 122–129; Edwin Roeder; published by Oct. 1987.

*Primary Examiner*—Tom Noland

[57] ABSTRACT

Method and apparatus are provided for analyzing fluid inclusions. A sectioned mineral sample is mounted and placed in a vacuum chamber. An optical microscope is used to examine the sample through a window in the vacuum chamber to identify a single fluid inclusion. A stylus in the vacuum chamber is manipulated by the operator to urge the diamond stylus against the identified fluid inclusion thereby rupturing the same. The gases, including evaporated volatile liquids, released from the inclusion are analyzed by a mass spectrometer.

24 Claims, 7 Drawing Sheets

FIG.1 — PRIOR ART

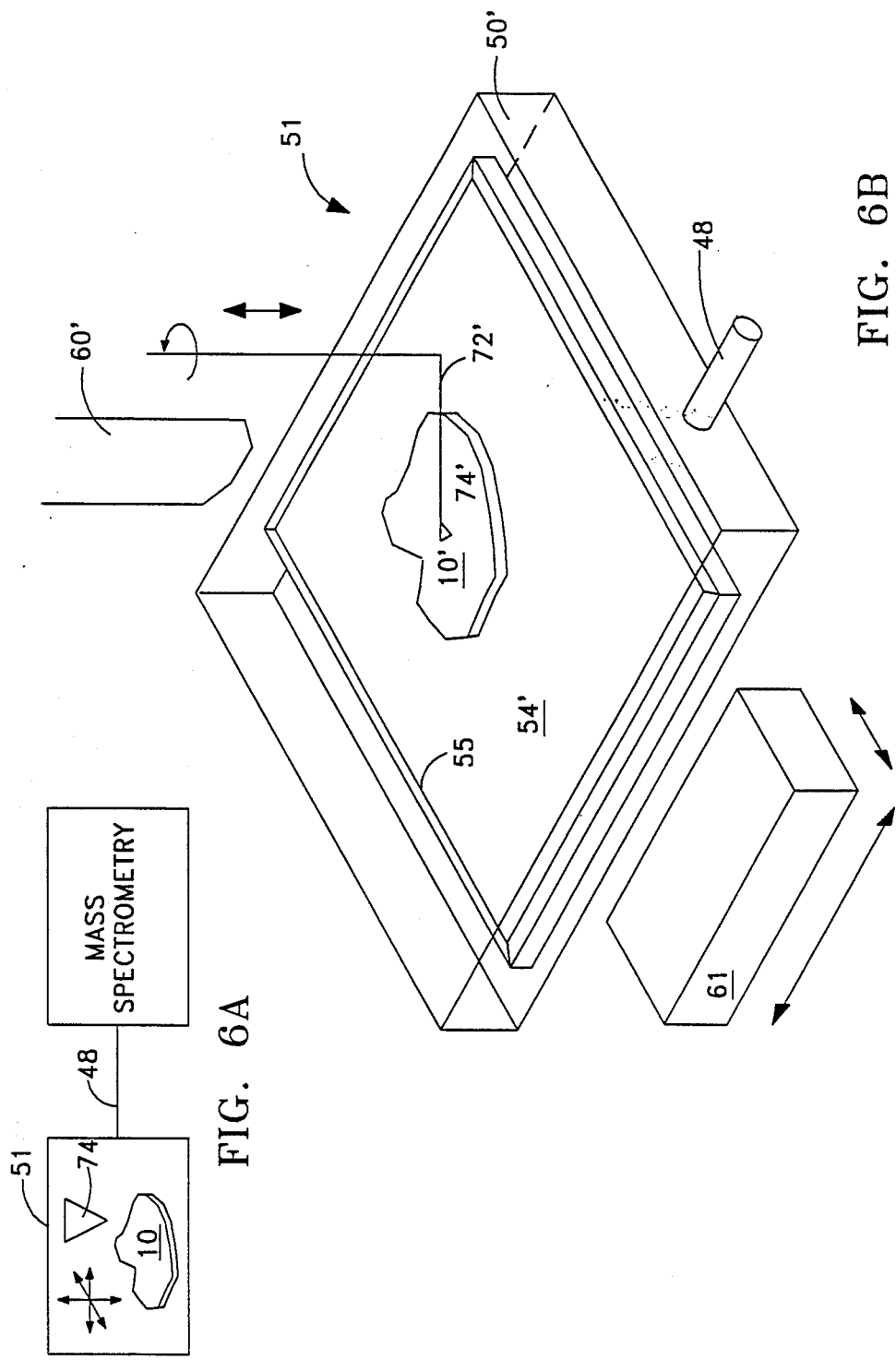

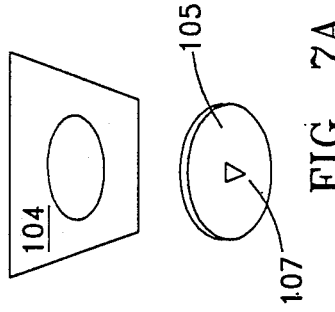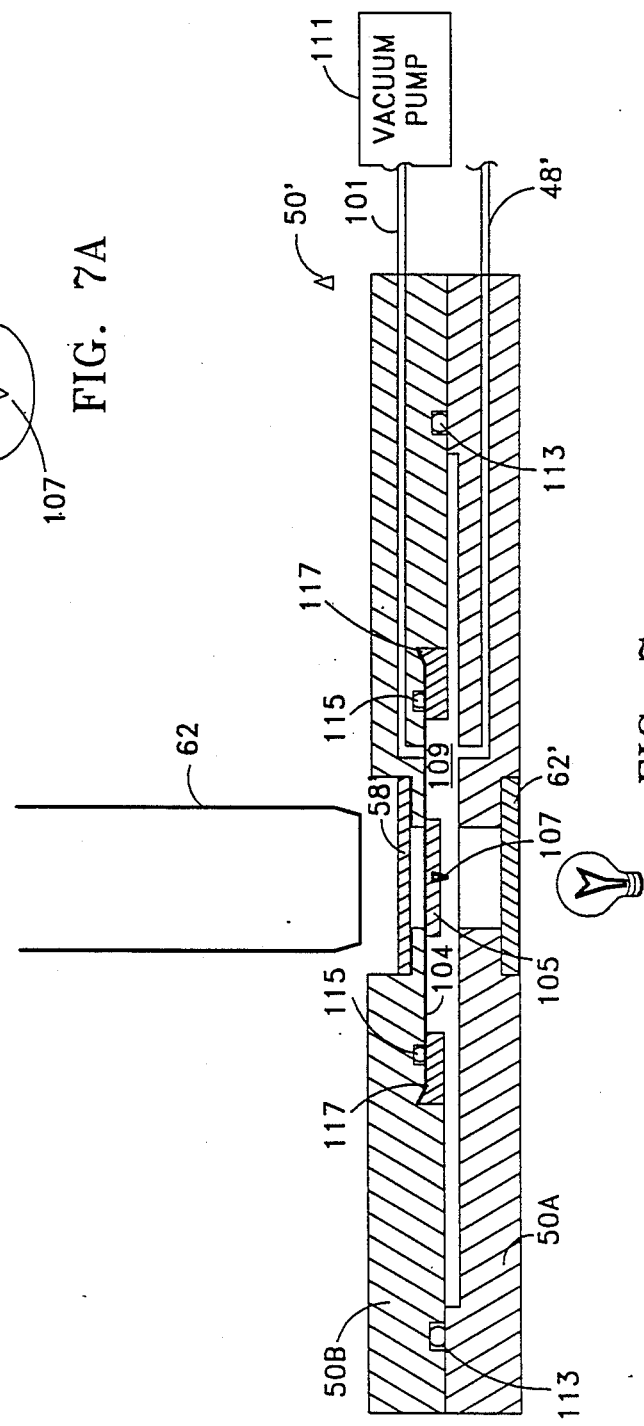

SAMPLE CHAMBER AND SYSTEM FOR ANALYZING FLUID INCLUSIONS

BACKGROUND OF THE INVENTION

1. Field of the Invention

The instant invention relates to methods and apparatus for analyzing fluid inclusions and more particularly to such methods and apparatus in which a fluid inclusion formed in a material such as mineral, glass, semiconducting material, and the like is ruptured and the gases released therefrom are analyzed.

2. Setting of the Invention

When natural minerals are formed, fluid present in the vicinity of the crystal may be trapped in microscopic defects known as fluid inclusions. These fluid inclusions may be ruptured to release the paleofluids contained therein in order to analyze the same. Such analysis can be used to determine information relating to the nature of the fluids present when the mineral was formed.

Analysis of fluid inclusions formed in sedimentary environments can yield information which is useful in the exploration for and production of oil and gas. For example, such studies can produce information relating to timing of hydrocarbon migration relative to rock formation, pathways of hydrocarbon migration, and the influence of hydrocarbons on rock formation.

Fluid inclusions in minerals may be formed at the time of mineral growth or they may form later when cracks in the mineral heal. Fluid inclusions formed at the time of initial mineral growth are referred to as primary inclusions and those formed during healing of cracks in the already-formed mineral are known as secondary inclusions. Cracks which have formed and healed at different times in the mineral's past produce different generations of secondary inclusions which trap environmental fluids present at the time of healing of the crack.

Sometimes a mineral overgrowth which acts as a cement may form between and around previously-formed mineral growth. Environmental fluids may also be trapped in fluid inclusions formed in the cement.

In the past, a number of different techniques have been utilized to release fluids from the inclusions in minerals and in other substances, such as glass. Such techniques include crushing and drilling. In another technique, the material, for example, a naturally-occurring mineral, is heated thereby increasing the fluid pressure in the fluid inclusions until the same rupture thereby releasing the fluids. This technique is known in the art as thermal decrepitation. A related technique involves use of a laser beam. When the laser beam is directed toward an area of interest in the mineral, the fluids in the inclusions are heated thereby rupturing the inclusions and releasing the fluids.

In the past, mass spectrometers have been used to analyze gases released from fluid inclusions using one of the above-described prior art techniques. Typically, the gases are released by cutting or crushing the mineral or by thermal decrepitation. Whatever the technique for releasing the gas, the gases are released into a vacuum which is in communicaiton with the mass spectrometer. When the fluids are released from the inclusions into the vacuum, the volatile liquids in the inclusions evaporate. The gases are provided directly to the mass spectrometer where they are ionized and thereafter qualitatively and/or quantitatively analyzed in the usual manner. The mass spectrometer may be used to analyze the chemistry of the gases and evaporated volatile liquids and/or to analyze the isotopic ratios of elements contained therein.

A problem exists with the various prior art methods for releasing fluids from inclusions in naturally occurring minerals and the like. When utilizing techniques such as crushing, slicing, and drilling, invariably fluids from more than one inclusion are released substantially simultaneously. This is especially true when dealing with small inclusions. For example, fluid inclusions of interest in sedimentary minerals are typically less than 10 microns in diameter. Thus, the analysis undertaken, whether by mass spectroscopy of by other means, may be of a plurality of fluid inclusions. Moreover, the analyzed fluids may be from inclusions formed at vastly differing times, such as a mixture of primary and secondary inclusions or a mixture of different generations of secondary inclusions.

Also, the mineral sample to be analyzed may include a plurality of different minerals closely adjacent one anotehr as well as mineral growth formed between and on the various minerals, all of which include fluid inclusions. When such a sample is crushed, sliced or drilled, fluids from inclusions in different minerals or from one or more cements may be simultaneously released. Such techniques prevent accurate analysis of selected types of inclusions such as inclusions from a particular mineral or cement or such as only primary inclusions, only secondary inclusions, or only a selected generation of secondary inclusions.

Some theorize that when fluids are released from inclusions in naturally occurring minerals by thermal decrepitation, single inclusions sequentially burst in response to increasing temperature. However, there is no known way to verify this. Data generated by mass spectroscopy analysis of gases, including evaporated liquids, released from fluid inclusions may be interpreted to mean that (a) only a single inclusion ruptured at a specified temperature or (b) groups of inclusions ruptured at a specified temperature.

Even if it could be verified that only a single inclusion at a time bursts as temperature is increased, this technique does not permit selection of a single identified inclusion nor does it permit selection of one inclusion from among a class of characterized inclusions, such as primary inclusions, secondary inclusions, a selected generation of secondary inclusions, inclusions from a selected cement, etc. In other words, as the temperature increases, any of the inclusions in the sample being tested may rupture and there exists no control over selection of a particular fluid inclusion or a fluid inclusion from among a particular class of inclusions to be ruptured.

The laser technique suffers from similar drawbacks. Typically, a selected area in a mineral sample is located using a microscope. Thereafter, a laser beam is shined through the microscope onto the sample and the heat generated thereby ruptures inclusions in the general area. Although the laser technique allows exercise of greater control over which inclusions are to be ruptured than thermal decrepitation of the entire sample, the heat produced by the laser beam is applied to a general area of the sample, and it is not possible to limit the technique to rupture only a single selected inclusion. Thus, the above described drawbacks of the thermal decrepitation technique are also present when a laser is used to release gases, including evaporated volatile liquids, from fluid inclusions. In addition, the laser heat can also release gases from volatile matter received in cracks in the sample or from adsorbed fluid in the sample. Further, pyrolysis of the minerals themselves can occur. Therefore, at least some of the analyzed gas will most likely be from sources other than fluid inclusions.

It is desirable to sample and analyze the content of selected individual fluid inclusions. The sensitivity threshold of mass spectrometers is dependent on the total volume occupied by the sample in the ionization chamber of the mass spectrometer and in the sample acquisition apparatus. Hence, it is desirable to maintain the volume of the sample acquisition apparatus small to permit effective analysis of the smaller fluid inclusions.

There exists a need for a method and apparatus for analyzing fluid inclusions in which a single identified fluid inclusion may be ruptured.

There exists a need for such a method and apparatus which maintains the volume of sample acquisition apparatus small so as to permit effective analysis of smaller fluid inclusions.

There exists a need for such a method and apparatus in which selected fluid inclusions from an identified class of inclusions may be selectively ruptured.

There exists a further need for such a method and apparatus in which a plurality of identified fluid inclusions may be individually and sequentially mechanically ruptured.

SUMMARY OF THE INVENTION

According to the invention, there is provided a sample taker for analysis of individual fluid inclusions of a rock specimen. The sample taker comprises an enclosed chamber for receiving a rock specimen and for collecting a sample of a fluid inclusion therein upon rupture thereof. Within the chamber, rupturing means is provided for mechanically rupturing a fluid inclusion.

According to further aspects, the invention can comprise an enclosed chamber having a space therein for receiving a module supporting a specimen, can comprise positioning means wholly external to the sample taker for positioning the module within the chamber, can comprise rupturing means comprising a stylus within the chamber for mechanically rupturing a fluid inclusion, can comprise such rupturing means comprising a diaphragm connected to the stylus for causing the stylus to rupture a fluid inclusion responsive to pressure exerted on the diaphragm, can comprise such rupturing means where the pressure exerted on the diaphragm is a fluid pressure, and can comprise the various other aspects and features of the invention herein described.

BRIEF DESCRIPTION OF THE DRAWINGS

Additional advantages associated with the instant invention will become more fully apparent when the following detailed description is read in view of the accompanying drawings, wherein:

FIG. 6A is a schematic illustration of a sample taker and mass spectrometry means for analyzing the chemistry, for example, composition, of gases released and/or volatilized from a fluid inclusion in sample taker 51, or for analyzing the isotopic ratios of elements contained therein, in accordance with the invention; and FIG. 6B is a schematic view of a third embodiment of the sample taker in accordance with the invention.

FIG. 7 is an enlarged, somewhat schematic view, shown mostly in cross-section of the third embodiment of the sample taker in accordance with the invention; and FIG. 7A is an exploded view in perspective of the lower side of a diaphragm 104 and window 105 with stylus 107 as in FIG. 7.

DETAILED DESCRIPTION OF THE PREFERRED EMBODIMENTS OF THE INVENTION

Figure 1:
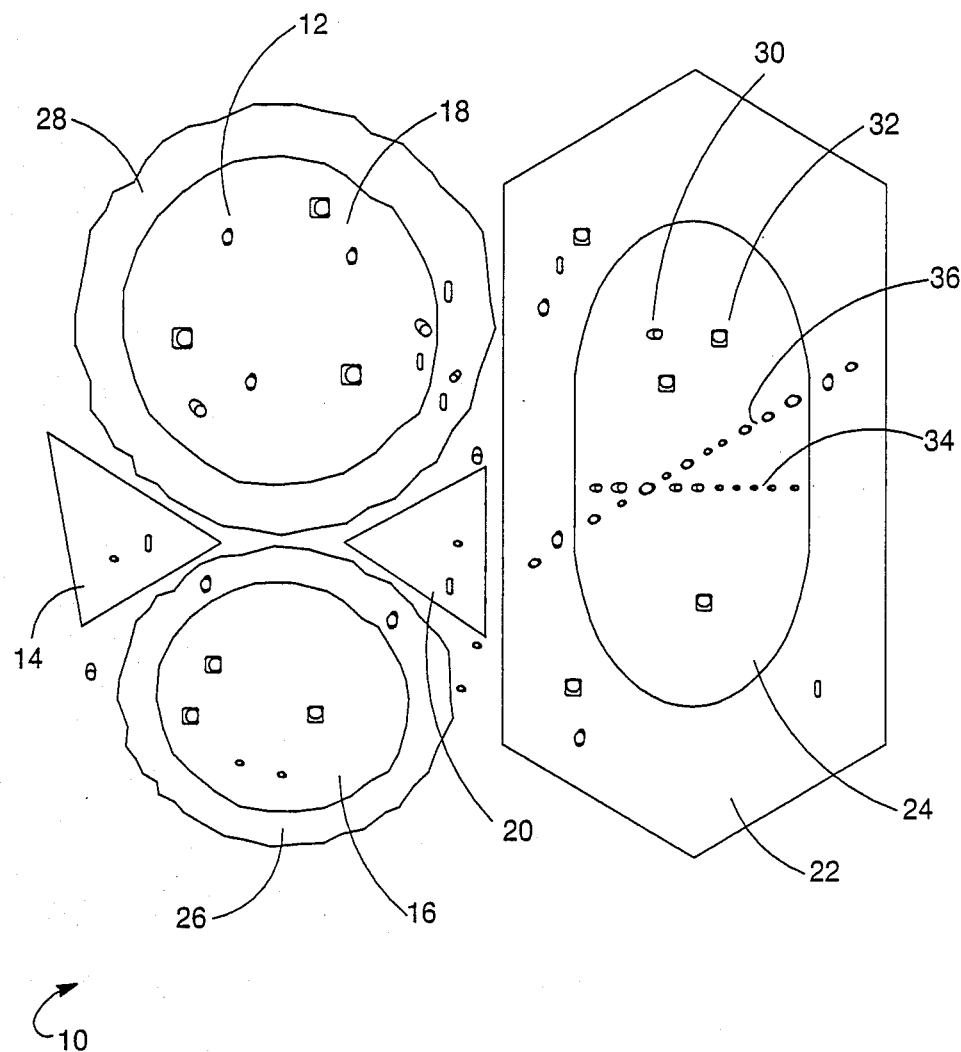
FIG. 1 is an enlarged view of a portion of a sectioned mineral sample containing a plurality of mineral growths as viewed through a microscope.

Turning now to the drawings and particularly to FIG. 1, consideration will now be given to an example of a mineral sample containing a plurality of mineral growths. Indicated generally at 10 is a portion of a sample extracted from naturally occurring mineral growth. Sample 10 consists of a cut section having a thickness of approximately 0.03–1.0 millimeter which is polished on both sides and which is mounted on a glass slide (not visible in FIG. 1). The view of FIG. 1 is a view of the polished section as seen through a microscope and is, thus, greatly enlarged. The approximate scale can be indicated in that substantially all of the fluid inclusions, like inclusion 12, formed in the various mineral growths in sample 10 are under 10 microns in diameter. Sample 10 includes a plurality of mineral growths, like minerals 14, 16, 18, 10, 22, and 24. Minerals 16 and 18 each include a mineral overgrowth 26 and 28, which acts as and is referred to herein as a cement.

Mineral 24 includes therein a plurality of primary inclusions, like inclusions 30 and 32. These inclusions were formed during the initial growth of mineral 24. A healed crack 34 is formed in mineral 24, and a healed crack 36 is formed in mineral 22 and in mineral 24. Crack 34 was formed in mineral 24 after the original growth of mineral 24, and thus after the primary inclusions, like inclusions 30 and 32 were formed. Crack 36 was also formed in minerals 22 and 24 after the formation of the primary inclusions in both minerals 22 and 24. Each of cracks 34 and 36 have a plurality of secondary inclusions, as shown, formed therealong. These secondary inclusions were formed during healing of cracks 34 and 36 when mineral growth developed in the cracks. It is to be appreciated that the secondary inclusions in crack 34 trap environmental fluids at a later time than the primary inclusions in mineral 24 and the secondary inclusions along crack 36 trap such fields at a later time than when the environmental fluids were trapped in the primary inclusions in both minerals 22 and 24. Moreover, the secondary inclusions in crack 34 may well be formed at a time far removed from those formed in crack 36, and thus, the secondary inclusions in crack 34 may be of a different generation than those along crack 36. Likewise, the primary inclusions formed in the various minerals and cements in sample 10 may be formed at vastly different items from one another, thus, trapping the environmental fluids present at the time of formation.

It should be noted that sample 10 may be taken from a portion of naturally occurring mineral growth using the usual sawing and polishing techniques. After the sample is cut, polished, and mounted on a slide, the same may be observed through a microscope to obtain the view of FIG. 1. Geologists are able to identify, by observation through microscope, various types of minerals. Such identification is based on well known criteria of shape of mineral growth and various optical properties. In addition, the fluid inclusions themselves can be classified in different ways such as the above described primary and secondary fluid inclusions. Other categories of inclusion classifications may be utilized; however, most common is classifying by origin, namely, primary and secondary inclusions. Such inclusions may be characterized by observation of the sample through the microscope.

Figure 2:
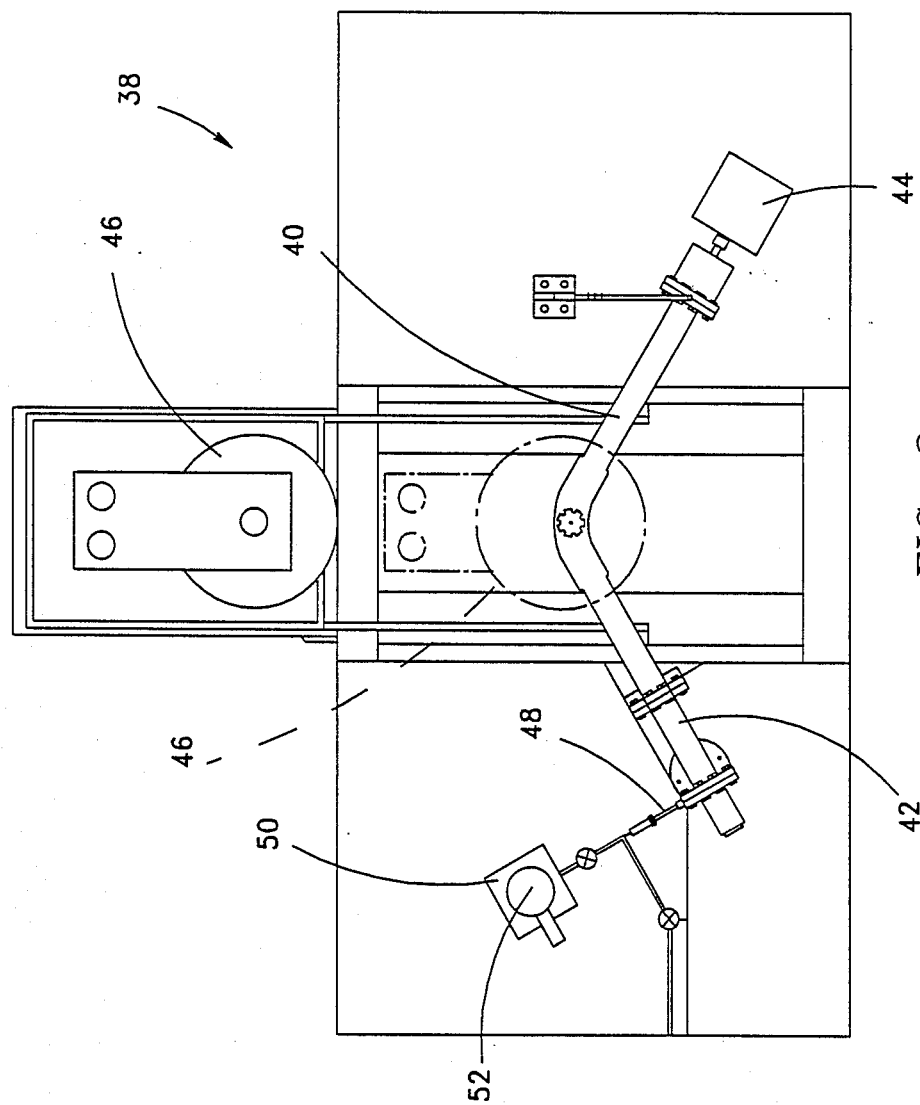
FIG. 2 is a top plan view of one embodiment of apparatus for analyzing the contents of fluid inclusions in accordance with the instant invention.
Figure 3:
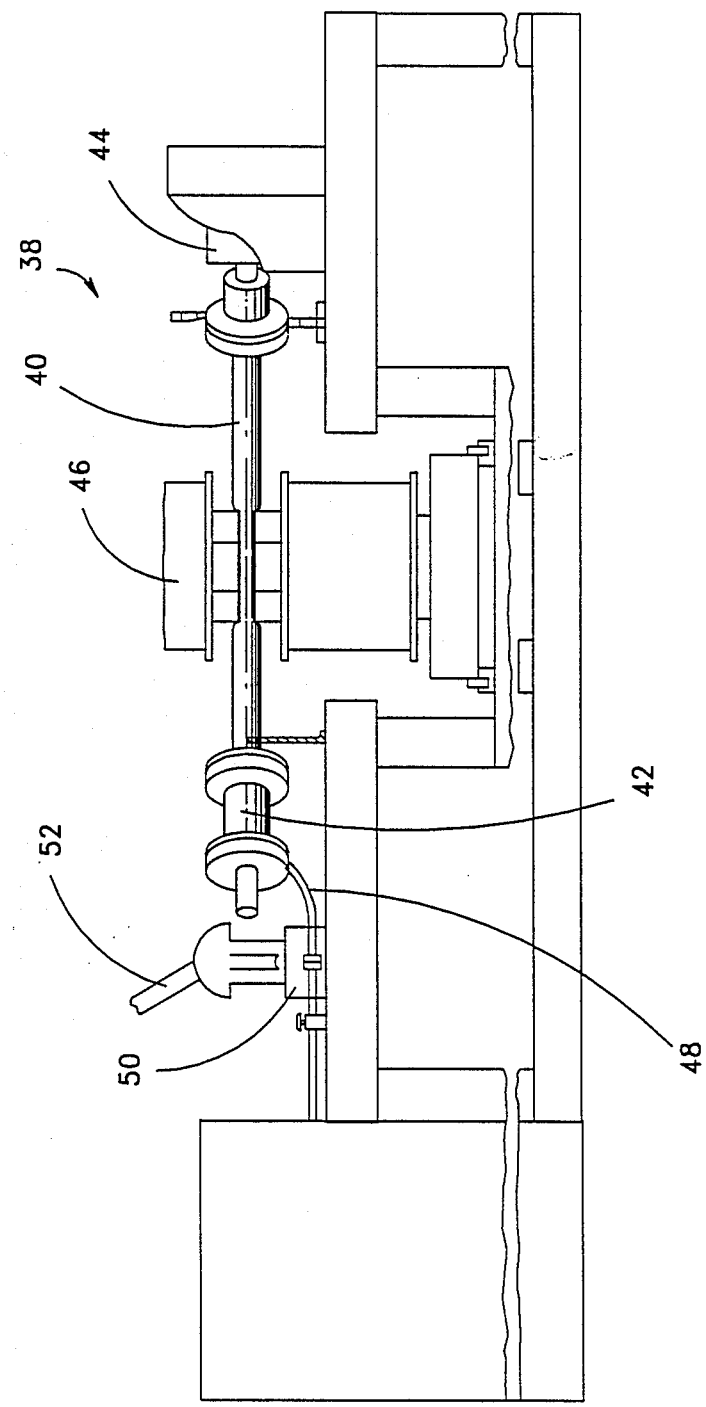
FIG. 3 is a front view of the apparatus shown in FIG. 2.

Turning now to FIGS. 2 and 3, indicated generally at 38 is one embodiment of apparatus for analyzing the contents of fluid inclusions in accordance with the instant invention. Included, therein, is a tube 40 having an ionization chamber 42 mounted on one end thereof, and an ion detector 44 mounted on the other end thereof. A magnet 46 is shown in a solid line position in FIG. 2 removed to the rear of tube 40 and in a dashed line position about tube 40. A tube 48 is in communication with ionization chamber 42 and provides a gas sample to the ionization chamber for analysis. In operative condition, a vacuum pump (not shown) maintains a substantial vacuum in tube 40.

That portion of the apparatus, shown in FIGS. 2 and 3 which has been described above, comprises a commercially available gas spectrometer, such being also referred to herein as means for analyzing gases. Generally speaking, the gas spectrometer operates as follows:

A gas sample to be analyzed is provided to ionization chamber 42 via tube 48. In the ionization chamber, an electron beam ionizes the gases which are then accelerated by an electric field along tube 40 toward magnet 46. The magnetic field alters the direction of travel of the ions in tube 40 depending upon the electrical charge and mass of each ion and upon the strength of the magnetic field. Ions of a certain mass-to-charge ratio travel around the bend in tube 40 toward detector 44. Other ions strike the walls of tube 40 and are not ultimately detected. The foregoing description of the operation of the mass spectrometer describes, in general, the operation of commercially available mass spectrometers. Such mass spectrometers may be used to analyzed gases present and to analyze isotope ratios of elements in the gases.

Vacuum chamber 50 is in fluid communication with ionization chamber 42 via tube 48. A commercially available microscope 52 is positioned over vacuum chamber 50. For a more detailed view of vacuum chamber 50, attention is directed to FIG. 4.

Chamber 50 is in fluid communication with ionization chamber 42 via tube 48. As mentioned, tube 40 of the mass spectrometer is maintained in a substantial vacuum by a pump (not shown) and thus tube 48 and chamber 50 are also are maintained in a vacuum.

Figure 4:
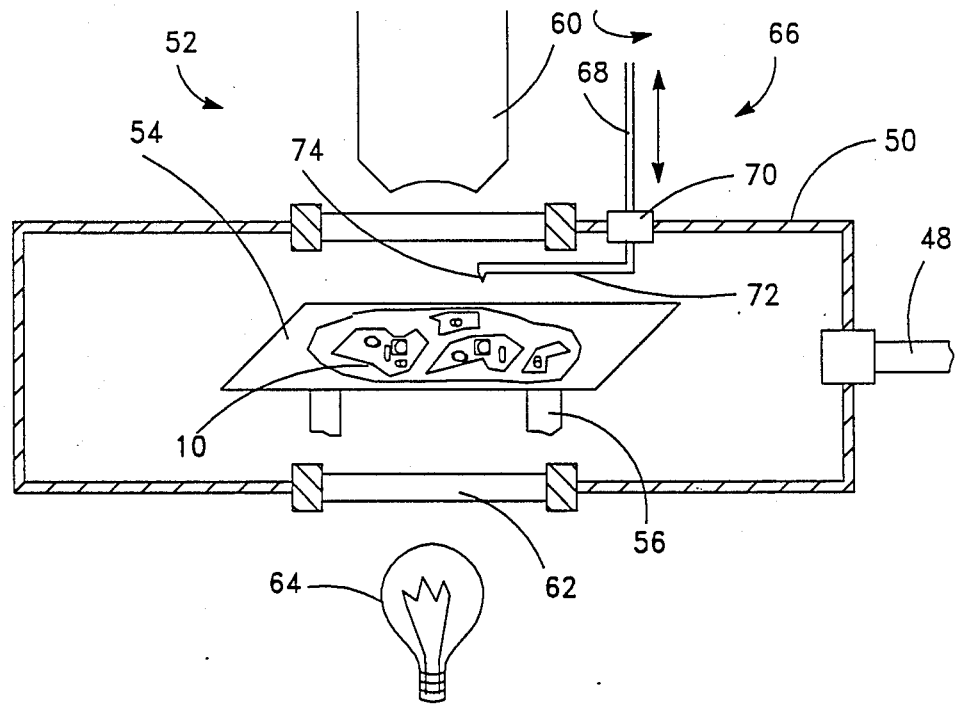
FIG. 4 is an enlarged somewhat schematic view, shown partly in cross-section, of a first embodiment of a sample taker in accordance with the invention.

Sample 10, as will be recalled, is mounted on a glass slide 54, which is viewable in FIG. 4. Slide 54, in the view of FIG. 4, is tilted forward to show sample 10. In operative condition, the slide is substantially parallel to the upper and lower walls of chamber 50. Slide 54 is removably mounted on a commercially available manipulator 56 which enables the slide to be moved laterally and vertically responsive to a commercially available operator control (not shown) for the manipulator. Chamber 50 includes a glass window 58 formed in an upper wall thereof over which is positioned a lower wall of vacuum chamber 50 beneath window 58. A light 64 is positioned beneath window 62.

Indicated generally at 66 is a rotary linear feedthrough. Feedthrough 66 includes a shaft 68 which extends through a seal 70. The lower end of the shaft 68 which is connected to an arm 72. A diamond stylus 74 is mounted on the end of arm 72 and is positioned so that a point formed thereon is directed downwardly.

Shaft 68, when rotated under operator control, imparts rotary motion to arm 72 about the axis of shaft 68. Also, the operator may raise and lower shaft 68 to effect raising and lowering of arm 72.

Figure 5:
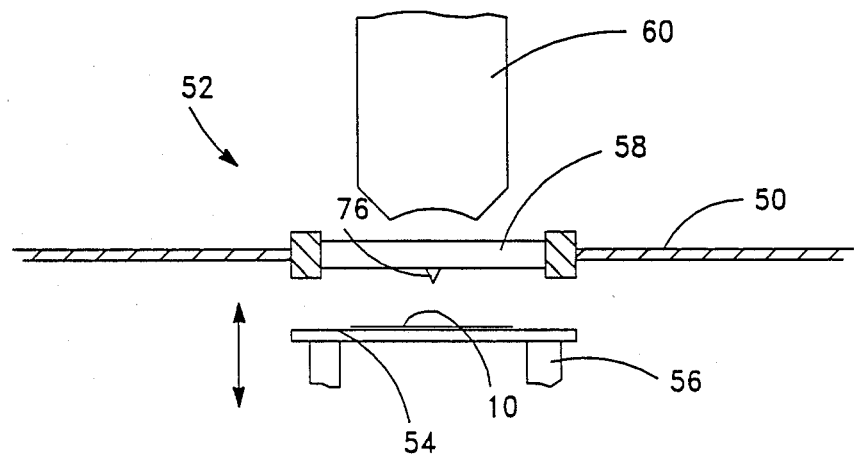
FIG. 5 is a schematic view similar to FIG. 4 of a second embodiment of the sample taker in accordance with the instant invention.

Attention is next directed to FIG. 5, wherein the structure previously identified with a numeral herein retains the same number in FIG. 5. In the embodiment of FIG. 5, a diamond stylus 76 is mounted directly on the underside of window 58 above sample 10 with a point formed on the stylus being directed downwardly.

Referring now to FIG. 6A, there is illustrated schematically the vacuum chamber/sample taker 51 and mass spectrometry means for analyzing the chemistry, for example, chemical composition, of gases released and/or volatilized from a fluid inclusion, or for analyzing the isotopic ratios of elements contained therein.

Sample taker 51 in FIG. 6A illustrates a stylus 74 for mechanically rupturing a fluid inclusion of sample 10, the stylus 74 and the sample 10 capable of being moved relative to one another in each of three dimensions (indicated by the arrows) so as to enable positioning and rupturing to sample a selected inclusion of sample 10.

The contents of the inclusion as well as any volatilized materials are provided by line 48 from vacuum chamber 51 for mass spectrometry. The mass spectrometer can be a commercially available mass spectrometer for separating a sample according to mass, and for collecting and measuring the various masses to determine composition and/or isotopic ratios of the sample introduced therein. Magnetic, quadrupole, time of flight or cycloidal analyzers can be used, as can magnetic and electric focusing.

Such mass spectrometers are widely used, as is known, for compound identification, elemental formula determination, molecular structure determination, quantitative mixture analyses, isotope ratio determination, and the like. Thus analyzers for use with the invention are readily available to those skilled in the art.

Referring now to FIG. 6B, FIG. 6B is a schematic view of a third embodiment of the sample taker/vacuum chamber in accordance with the invention. Reference numerals correspond to those described in FIGS. 4 and 5.

Thus, the sample taker indicated generally at 51 comprises vacuum chamber 50' having conduit 48 for providing a fluid sample to a mass spectrometer (see FIG. 6A). The chamber 50' has a space therein for receiving slide 54' on which is suppported specimen 10'. Slide 54' has a band 55 of ferromagnetic material affixed thereto so that by movement of magnet 61, the module consisting of slide 54', band 55, and specimen 10' can be moved beneath microscope 60' to position the stylus 74' for rupturing a selected fluid inclusion by rotary linear feedthrough 72'. The sample taker can be mounted above the stage of a microscope and magnet 61 (of which there can be more than one to ensure good magnetic coupling with band 55) can be adapted to be manipulated by the usual microscope calipers.

Referring now to FIG. 7, FIG. 7 is an enlarged, somewhat schematic view shown mostly in cross-section of another embodiment of a portion of the apparatus shown in FIGS. 2 and 3. The sample taker comprises vacuum chamber 50' having portions 50A and 50B defining a space therebetween and capable of sustaining a vacuum and from which a fluid sample can be taken by tube 48 to a mass spectrometer (see FIG. 6A). A stylus 107 is affixed to window 105, for example, a quartz or sapphire window. The window 105 permits light to pass thru to assist in positioning a selected inclusion beneath the stylus for sampling. Window 105 is mounted, for example by brazing to diaphragm 104. Diaphragm 104 is in fluid communication with vacuum pump 111 by conduit 101 so that fluid pressure can be exerted on or removed from diaphragm 104. Normally a vacuum is applied to the upper side of diaphragm 104 and the diaphragm with window and stylus is held above a sample which can be received in chamber 109. When the vacuum is removed and air is permitted to enter diaphragm 104 causes stylus 107 to rupture a fluid inclusion selected by, for example, the action of magnet 61 on ferromagnetic strip 55 of slide 54 on which specimen 10 is supported (see FIG. 6B). Portions 50A and 50B can be sealed against fluid leakage by seal ring 113 so that a vacuum can be maintained in chamber 109. Diaphragm 104 can be mounted between portions 50A and 50B by sealing ring 115 and clamping ring 117. The assembly can be held together by any suitable means such as screws clamps, and the like (not shown). Windows 58' and 62' can be provided on opposite sides of the sample taker 50 so that light can be passed through a sample in chamber 109 for observation by microscope 60'. Window 105 likewise can allow light to be passed therethru for the same purpose.

Turning now to FIG. 7A, there is illustrated in exploded perspective view the lower side of diaphragm 104, window 105, and stylus 107. Diaphragm 104 can be flanged as shown so as to be mounted between sections 50A and 50B of sample taker 50' (see FIG. 7). Window 105' with stylus 107' is mounted on diaphragm 104, for example by brazing. The diaphragm can be made, for example, of stainless steel or other flexible non porous material and can have an opening therein so that light can be transmitted through windows 58', 62', and 105 as well a through a sample in chamber 109. When the vacuum applied by pump 111 is bled off, about one atmosphere of pressure can be exerted on the diaphragm causing stylus 107 to rupture a selected inclusion.

Figure 8:
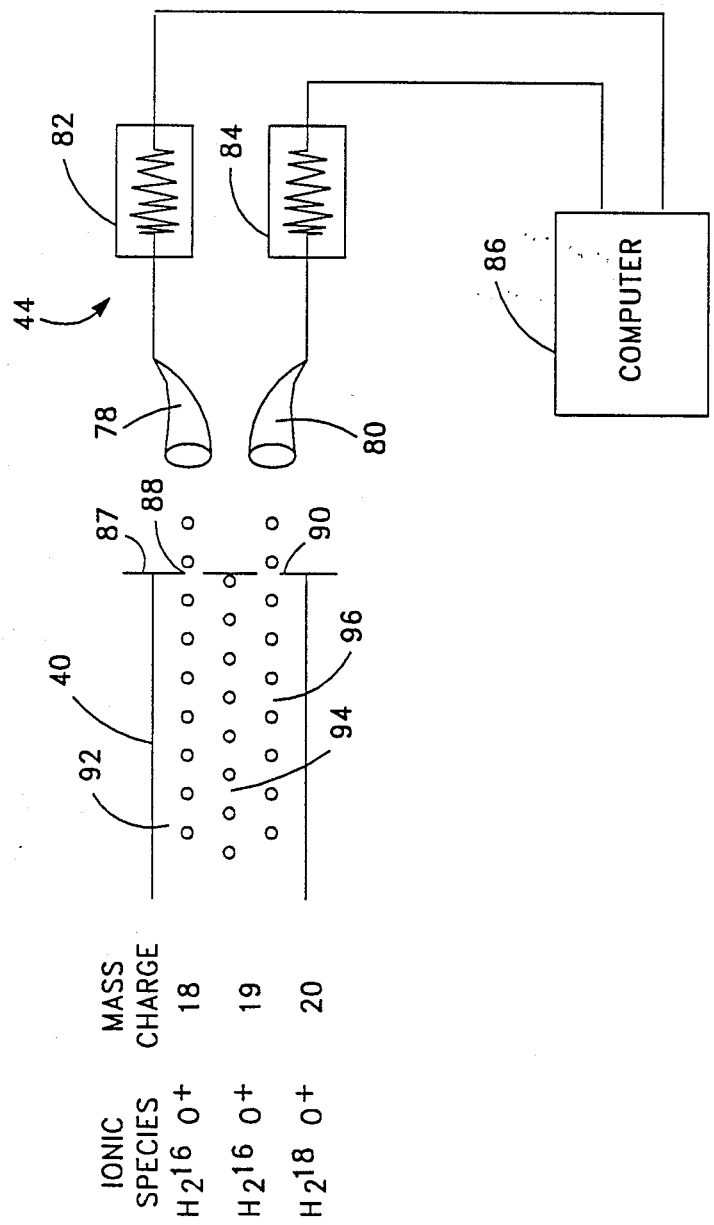
FIG. 8 is a schematic diagram of a portion of the apparatus of FIGS. 2 and 3.

Turning now to FIG. 8, one type of mass spectrometry in accordance with the invention is illustrated in which ion detector 44 includes therrein a pair of commercially available Galileo-type electron multipliers 78 and 80. Each of the electron multipliers is connected to an associated ion counter 82 and 84 which, in turn, are connected to a commercially available computer 86. the end of tube 40, which is directed toward ion detector 44, includes an end plate 87 having slits, such as slits 88 and 90 formed therein. End plate 87 may be fixed in selected positions relative to tube 40 thereby varying the radial position of the slits relative to the longitudinal axis of tube 40.

Consideration will now be given to the operation of the instant embodiments of the invention. When a mineral growth of interest is located, sample 10 is prepared in the usual fashion. A slice is taker from the mineral growth and is thereafter polished and mounted on glass slide 54, as shown in FIGS. 4 and 5. Thereafter, slide 54 is mounted on manipulator 56 and light 64 is turned on. An operator examines sample 10 through microscope 52 and positions the same beneath the microscope lens using the controls (not shown) for manipulator 56. The operator searches for a class of fluid inclusions of interest, for example, the secondary inclusions along healed crack 36 in FIG. 1. Next a single fluid inclusion of interest is identified. Feedthrough 66 is manipulated by rotation of shaft 68 until stylus 74 is above the identified fluid inclusion. Manipulator 56 may also be moved in order to position the slide relative to stylus 74.

When the feedthrough and slide are positioned as described above, shaft 68 is urged downwardly until diamond stylus 74 punctures the identified fluid inclusion thereby releasing gases and evaporated volatile liquids from the inclusion. It is to be appreciated that fluid inclusions may include mixtures of gases and liquids, and in some cases solids. Volatile liquids are those which evaporate when exposed to the vacuum within chamber 50.

The opening of the inclusion is by mechanical rupturing using the sharp fine point of a stylus, for example, a diamond stylus. Such mechanical rupturing as used herein can mean that the inclusion is pricked or pinked or lanced or spiked or punctured or pierced or punched by the sharp point of the stylus; but is not intended to encompass opening of inclusions by slicing, crushing, boring, or drilling since such are not effective for sampling individual inclusions of the size comtemplated by the invention.

When the inclusion is so ruptured, the gases released from the inclusion, including the evaporated volatile liquids, pass through tube 48 to ionization chamber 42 where the same are ionized. The ionized gases are accelerated in tube 40 toward magnet 46 which changes the direction of travel of the ionized gases.

Most fluid inclusions of interest in connection with exploration and production of oil and gas are water dominated. Both chemical composition and isotopic ratios of contained and/or volatilized compounds can be determined in accordance with the invention. In water, the isotope ratios of most interest, and those which have the best chance of being analyzed, are $^{16}O/^{18}O$ $^{1}H/^{2}H$. These ratios can be determined by detecting the following ionic species: $H_2^{16}O+$, $HD^{16}O+$, and $H_2^{18}O+$.

The mass spectrometer is adjusted, by adjusting the power of magnet 46, so that ionic species having a mass to charge ratio of 18, 19, and 20, namely, $H_2^{16}O+$, $HD^{16}O+$, and $H_2^{18}O+$, strike end plate 87.

In FIG. 8, a first ion stream 92 is made up of $H_2^{16}O+$ ions: a second stream 94 is made up of $HD^{16}O+$ ions, and a third ion stream 96 is made up $H_2^{18}O+$ ions. Because each ion stream is made up of ions having a different mass-to-charge ratio, the effect of magnet 46 on the ions is to separate them into very slightly nonparallel streams of ions, each of which strikes end plate 87 in a predetermined location. It can, thus, be seen that by selectively positioning end plate 87 and electron multiplier 78 and 80, an ion stream made up of ions having a selected mass-to-charge ratio may be directed into one of the electron multipliers, while the other ions are absorbed in end plate 87. Each ion in, for example, ion stream 92, which passes through slit 88 and strikes electron multiplier 78 generates a shower of secondary electrons in multiplier 78 which is provided to ion counter 82. Each electron shower is counted by counter 82 as a single ionization event which is recorded by computer 86.

Detector 44 is advantageous when dealing with a very small gas sample, such as that which is released from a single fluid inclusion. Since electron multipliers do not necessarily release the same number of electrons in response to ions having the same mass-to-charge ratio, use of the ion counters to convert each electron shower into a single ionization event increases the accuracy of the collected data. It can be seen that by shifting end plate 87 and electron multiplier 78 and 80, different selected ion streams may be detected. Furthermore, by changing the strength of the magnetic field generated by magnet 46, streams of ions having different mass-to-charge ratios than those shown in the example may be made to strike end plate 87 and/or pass through the slits therein.

Referring now to FIG. 5, in the operation of the embodiment shown therein, slide manipulator 56 is positioned until the fluid inclusion of interest is directly beneath diamond stylus 76. Thereafter, the controls (not shown) for manipulator 56 are operated to drive manipulator 56, and thus sample 10 directly upwardly into diamond stylus 76. Such ruptures the fluid inclusion positioned beneath the diamond stylus and permits the gases released therefrom to be analyzed, as described above. In operation of the embodiment of FIG. 5, an operator uses miroscope 52 in the same manner as the embodiment of FIG. 4 to characterize a class of inclusions and to thereafter identify a particular inclusion for rupture in order to analyze the gases released therefrom.

Each diamond stylus 74 and 76 includes a point sufficient to puncture fluid inclusions less than 10 microns in diameter.

It can, thus, be seen that the instant invention permits characterizing a class of fluid inclusions such as primary or secondary inclusions, for example, by observation (in the instant embodiment of the invention with an optical microscope) and thereafter identifying a single inclusion within the characterized class. The identified inclusion may then be ruptured and the gases released therefrom analyzed to derive information relating to the geologic process which formed the mineral containing the fluid inclusion.

The instant invention may, therefore, be used to verify whether or not prior art techniques for analyzing gases released from fluid inclusions, such as thermal decrepitation, are, in fact, sequentially and individually releasing gases from fluid inclusions, as is theorized by some. Moreover, the instant invention permits selecting a single particular identified fluid inclusion for rupturing in order to analyze gases released therefrom so that data from a particular characterized class of inclusions may be generated. Generating such data was not possible with the prior art techniques for releasing gases from fluid inclusions.

It is to be appreciated that additions and modifications may be made to the embodiments of the invention disclosed herein without departing from the spirit of the same which is defined in the following claims.

What is claimed is:

1. A sample taker for analysis of individual fluid microinclusions having diameters under 10 microns of a rock specimen comprising:
    an enclosed chamber for receiving the rock specimen and for collecting fluid microinclusion samples upon microinclusion rupture;
    the enclosed chamber comprising means for transmitting light through the rock specimen within the enclosed chamber; and
    the enclosed chamber further comprising means for viewing the rock specimen using a microscope for selecting fluid microinclusions for rupturing; and
    within the chamber, microrupturing means for individually mechanically rupturing single selected fluid microinclusions of the rock specimen having diameters under 10 microns;
    the microrupturing means comprising a stylus having a point sufficient to puncture individual fluid microinclusions less than 10 microns in diameter;
    also within the chamber, positioning means for positioning single selected fluid microinclusions of the rock specimen for rupturing by the microrupturing means; and
    also within the chamber, drive means for causing the microrupturing means to mechanically rupture single selected fluid microinclusions.

2. The sample taker of claim 1 wherein:
    the enclosed chamber has a space therein for receiving a module supporting the rock specimen; and further comprising
    conduit means for providing any collected fluid microinclusion samples to means for analysis thereof.

3. The sample taker of claim 1
    wherein the drive means is responsive to operator control for causing the stylus to mechanically rupture single selected fluid microinclusions of the rock specimen.

4. The sample taker of claim 1 wherein
    the rupturing means comprises a diaphragm having the stylus connected thereto for microrupturing single selected fluid microinclusions responsive to fluid pressure exerted on the diaphragm.

5. The sample taker of claim 4 wherein:
    the diaphragm comprises a window; and
    the stylus is mounted on the window for rupturing a fluid inclusion responsive to fluid pressure exerted on the diaphragm.

6. The sample taker of claim 1 further comprising:
    a module comprising a ferromagnetic material for supporting the rock specimen; and wherein
    the enclosed chamber is constructed of nonferromagnetic materials.

7. The sample taker of claim 1 wherein:
    the enclosed chamber comprises a vacuum chamber for receiving the rock specimen therein and having a conduit therefrom for conducting fluid from the vacuum chamber.

8. The sample taker of claim 7 further comprising:
    a first window on a first side of the enclosed chamber and a second window on a second side of the enclosed chamber for permitting light to be transmitted from the first side to the second side of the enclosed chamber.

9. The sample taker of claim 1 wherein:

the stylus is mounted on and inside the enclosed chamber; and the drive means comprises means for driving the rock specimen into the stylus for puncturing single selected fluid microinclusions.

10. The sample taker of claim 1 wherein:

the drive means comprises a rotary feedthrough extending through a wall of the enclosed chamber;

said stylus mounted to and controlled by the rotary feedthrough.

11. The sample taker of claim 1 wherein:

the means for transmitting light comprises windows on opposing sides of the enclosed chamber for permitting light to pass through the rock specimen;

the stylus is mounted on and inside one of the windows; and the drive means comprises means for driving the rock specimen into the stylus for rupturing single selected fluid microinclusions.

12. Apparatus for sample collecting comprising:

a sample taker comprising an enclosed chamber for receiving a rock specimen and for collecting a fluid inclusion sample upon fluid inclusion rupture, the sample taker further comprising rupturing means within the enclosed chamber for mechanically rupturing a single selected fluid inclusion of the rock specimen;

positioning means within the enclosed chamber of the sample taker for positioning the rock specimen within the enclosed chamber relative to the rupturing means within the enclosed chamber for rupturing the single selected fluid inclusion; wherein the rupturing means of the sample taker comprises a diaphragm having a stylus connected thereto for rupturing the single selected fluid inclusion responsive to pressure exerted on the diaphragm.

13. The apparatus of claim 12 wherein:

the positioning means comprises a magnet, the module comprises a ferromagnetic material, and the enclosed chamber is constructed of nonferromagnetic materials.

14. The apparatus of claim 12 wherein:

the enclosed chamber is effective for receiving a module therein supporting the rock specimen; and further comprising conduit means for providing the collected sample of the single selected fluid inclusion from the enclosed chamber to means for analyzing the sample.

15. The apparatus of claim 12 wherein:

the rupturing means of the sample taker is responsive to operator control for causing the stylus to mechanically rupture the single selected fluid inclusion of the rock specimen.

16. The apparatus of claim 12 wherein the sample taker further comprises:

a module comprising a ferromagnetic material for supporting the rock specimen; and wherein the enclosed chamber is constructed of nonferromagnetic materials.

17. The apparatus of claim 12 wherein the sample taker further comprises:

means for transmitting light through the enclosed chamber for permitting viewing of the rock specimen using a microscope.

18. The apparatus of claim 17 wherein:

the enclosed chamber comprises a vacuum chamber for receiving the rock specimen therein and having a conduit therefrom for conducting fluid from the vacuum chamber.

19. The apparatus of claim 18 wherein the sample taker further comprises:

a first window on a first side of the enclosed chamber and a second window on a second side of the enclosed chamber for permitting light to be transmitted from the first side to the second side of the enclosed chamber.

20. The apparatus of claim 17 wherein:

the means for transmitting light comprises windows on opposing sides of the enclosed chamber for permitting light to pass through the rock specimen;

said stylus is mounted on and inside one of the windows; and the drive means comprises means for driving the rock specimen into the stylus for rupturing single selected fluid inclusions.

21. The apparatus of claim 12 wherein:

the rupturing means within the enclosed chamber comprises microrupturing means for mechanically rupturing single fluid microinclusions having diameters under 10 microns and drive means for causing the microrupturing means to mechanically rupture single selected fluid microinclusions.

22. The apparatus of claim 21 wherein:

the microrupturing means comprises said stylus, said stylus having a point effective for puncturing fluid microinclusions in a rock specimen having diameters under 10 microns.

23. The apparatus of claim 21 wherein:

the microrupturing means comprises said stylus, said stylus mounted on and inside the enclosed chamber; and the drive means comprises means for driving the rock specimen into the stylus for puncturing single selected fluid microinclusions.

24. The apparatus of claim 12 wherein:

the diaphragm comprises a window; and said stylus is mounted on the window for rupturing the selected fluid inclusion responsive to fluid pressure exerted on the diaphragm.

* * * * *